US009412087B2

(12) United States Patent
Vollm et al.

(10) Patent No.: US 9,412,087 B2
(45) Date of Patent: Aug. 9, 2016

(54) SYSTEM, METHOD, AND APPARATUS FOR MAPPING PRODUCT IDENTIFICATION TO MEDICATION IDENTIFICATION

(71) Applicant: Aesynt Incorporated, Cranberry, PA (US)

(72) Inventors: James Vollm, Baden, PA (US); Chris Zollinger, Gibsonia, PA (US)

(73) Assignee: Aesynt Incorporated, Cranberry, PA (US)

( * ) Notice: Subject to any disclaimer, the term of this patent is extended or adjusted under 35 U.S.C. 154(b) by 227 days.

(21) Appl. No.: 14/195,246

(22) Filed: Mar. 3, 2014

(65) Prior Publication Data

US 2015/0248634 A1    Sep. 3, 2015

(51) Int. Cl.
| | | |
|---|---|---|
| G06F 19/00 | (2011.01) | |
| G06Q 10/00 | (2012.01) | |
| G06Q 30/00 | (2012.01) | |
| G06Q 90/00 | (2006.01) | |
| G06Q 10/08 | (2012.01) | |
| G06Q 50/22 | (2012.01) | |

(52) U.S. Cl.
CPC .............. *G06Q 10/087* (2013.01); *G06Q 50/22* (2013.01)

(58) Field of Classification Search
CPC ..... G06Q 10/087; G06Q 50/22; G06F 19/326
USPC ................................. 235/385, 375; 705/2, 28
See application file for complete search history.

(56) References Cited

U.S. PATENT DOCUMENTS

| | | |
|---|---|---|
| 3,868,634 A | 2/1975 | Dolch |
| 3,949,363 A | 4/1976 | Holm |
| 4,074,114 A | 2/1978 | Dobras |
| 4,075,461 A | 2/1978 | Wu et al. |
| 4,104,514 A | 8/1978 | Sherer et al. |
| 4,135,663 A | 1/1979 | Nojiri et al. |
| 4,253,018 A | 2/1981 | Amacher et al. |
| 4,308,455 A | 12/1981 | Bullis et al. |
| 4,402,088 A | 8/1983 | McWaters et al. |
| 4,414,468 A | 11/1983 | Laurer et al. |
| 4,421,978 A | 12/1983 | Laurer et al. |
| 4,533,825 A | 8/1985 | Yamada |
| 4,602,152 A | 7/1986 | Dittakavi |
| 4,717,818 A | 1/1988 | Broockman et al. |
| 4,728,784 A | 3/1988 | Stewart |
| 4,731,525 A | 3/1988 | Hice |
| 4,879,456 A | 11/1989 | Cherry et al. |

(Continued)

FOREIGN PATENT DOCUMENTS

WO        WO 91/06068 A1    5/1991

*Primary Examiner* — Laura Gudorf
(74) *Attorney, Agent, or Firm* — Alston & Bird LLP

(57) ABSTRACT

A method, system, and corresponding apparatus are provided for mapping product identification to medication identification. In particular, a method may include receiving a product identifier associated with a medication container; comparing the product identifier with a database of product identifier formats; and retrieving a medication identifier from the product identifier in response to the product identifier corresponding to a single product identifier format in the database. Methods may include applying an algorithm to the product identifier in response to the product identifier failing to correspond with a product identifier format in the database and creating a mapped product identifier to a single medication identifier in the database in response to the application of the algorithm to the product identifier resulting in the single medication identifier match.

17 Claims, 4 Drawing Sheets

(56) References Cited

U.S. PATENT DOCUMENTS

| | | | |
|---|---|---|---|
| 4,992,650 A | 2/1991 | Somerville | |
| 5,128,527 A | 7/1992 | Kawai et al. | |
| 5,144,118 A | 9/1992 | Actis et al. | |
| 5,189,289 A | 2/1993 | Watanabe | |
| 5,194,722 A | 3/1993 | Mergenthaler et al. | |
| 5,196,685 A | 3/1993 | Izumi | |
| 5,216,231 A | 6/1993 | Ouchi | |
| 5,227,617 A | 7/1993 | Christopher et al. | |
| 5,262,625 A | 11/1993 | Tom et al. | |
| 5,262,626 A | 11/1993 | Goren et al. | |
| 5,270,524 A | 12/1993 | Ouchi | |
| 5,298,731 A | 3/1994 | Ett | |
| 5,324,924 A | 6/1994 | Cai et al. | |
| 5,329,104 A | 7/1994 | Ouchi et al. | |
| 5,414,252 A | 5/1995 | Shinoda et al. | |
| 5,468,946 A | 11/1995 | Oliver | |
| 5,548,110 A | 8/1996 | Storch et al. | |
| 5,557,092 A | 9/1996 | Ackley et al. | |
| 5,629,511 A | 5/1997 | Iwaguchi et al. | |
| 5,675,137 A | 10/1997 | Van Haagen et al. | |
| 5,797,515 A | 8/1998 | Liff et al. | |
| 5,883,370 A | 3/1999 | Walker et al. | |
| 5,932,862 A | 8/1999 | Hussey et al. | |
| 6,095,419 A | 8/2000 | Watanabe et al. | |
| 6,098,892 A | 8/2000 | Peoples, Jr. | |
| 6,260,761 B1 | 7/2001 | Peoples, Jr. | |
| 2007/0179957 A1* | 8/2007 | Gibson | G06F 19/326 |
| 2014/0117081 A1* | 5/2014 | Jablonski | G06F 19/326 235/375 |

\* cited by examiner

SYSTEM, METHOD, AND APPARATUS FOR MAPPING PRODUCT IDENTIFICATION TO MEDICATION IDENTIFICATION

FIELD

Exemplary embodiments of the present invention relate generally to capturing information from an identification code and, in particular, to capturing the information and mapping the captured information to a product.

BACKGROUND

Recent advances in medical research have resulted in a proliferation of medication types and doses such that there are thousands of medications, doses, and related packaging that can flow through pharmacies, hospitals, and other healthcare facilities. As the number of available medications and doses increases, tracking these medications and doses with unique identifiers becomes a challenge. Further, changes in package quantities, doses, manufacturer, etc. can result in the unique identifier associated with each package changing. Additionally, when distributors or wholesalers have product shortages or changes in contracts, brands of medications may be interchanged in order to meet the demand of customers. While medication brands may be interchangeable, these different brands have different product identifiers that are not interchangeable, and a chain of events may be required by the customer to ensure that the substituted medication can be scanned throughout the enterprise to ensure accurate dispensing, charge capture, and inventory management.

It is important for a healthcare facility or pharmacy to properly identify medications that are received and processed. Medications may arrive and/or be distributed in a variety of package quantities, package form factors, and doses such that identification of the medication may be different between two different packages of the same medication. While standards exist for some facets of medication identification, such as the National Drug Code or NDC, products from different manufacturers may have differing product codes on a medication package for distinctions between package quantities, package form factors, or other differences.

BRIEF SUMMARY

In general, exemplary embodiments of the present invention provide an improvement over the known prior art by, among other things, providing a system and method for mapping product identification to medication identification.

In particular, according to one aspect of the present invention, a method is provided including receiving a product identifier associated with a medication container; comparing the product identifier with a database of product identifier formats; and retrieving a medication identifier from the product identifier in response to the product identifier corresponding to a single product identifier format in the database. Methods may include applying an algorithm to the product identifier in response to the product identifier failing to correspond with a product identifier format in the database and creating a mapped product identifier to a single medication identifier in the database in response to the application of the algorithm to the product identifier resulting in the single medication identifier match. Methods may optionally include generating a plurality of potential medication identifier matches in response to the product identifier corresponding to a plurality of product identifier formats in the database. Methods may include presenting the plurality of potential matches to a user, receiving a selection of one of the plurality of potential medication identifier matches to be a determined medication identifier match, and creating a mapped product identifier to the determined medication identifier match in the database in response to receiving the selection of the determined medication identifier match.

According to some embodiments, methods may include generating a list of medication identifiers irrespective of the product identifier in response to the application of the algorithm failing to result in a single medication identifier match and in response to the application of the algorithm failing to result in a plurality of potential medication identifier matches. Methods may include receiving a selection of one of the list of medication identifiers to be a determined medication identifier match, and creating a mapped product identifier to the determined medication identifier match in the database in response to receiving the selection of the determined medication identifier match. Receiving a product identifier associated with a medication container may include scanning a barcode from the medication container and deciphering the barcode to obtain the product identifier.

According to an example embodiment, an apparatus may be provided including at least one processor and at least one non-transitory memory including computer program code, the at least one memory and the computer program code configured to, with the processor, cause the apparatus to receive a product identifier associated with a medication container, compare the product identifier with a database of product identifier formats, and retrieve a medication identifier corresponding to the product identifier in response to the product identifier corresponding to a single product identifier format in the database. Embodiments may optionally apply an algorithm to the product identifier in response to the product identifier failing to correspond with a product identifier format in the database, and create a mapped product identifier to a single medication identifier match in the database in response to the application of the algorithm to the product identifier resulting in the single medication identifier match. The apparatus may optionally generate a plurality of potential medication identifier matches in response to the product identifier corresponding to a plurality of product identifier formats in the database. The plurality of potential medication identifier matches may be presented to a user. According to some embodiments, a selection may be received of one of the plurality of potential medication identifier matches to be a determined medication identifier match, and a mapped product identifier may be created to the determined medication identifier match in the database in response to receiving the selection of the determined medication identifier match.

According to some embodiments, the apparatus may generate a list of medication identifiers irrespective of the product identifier in response to the application of the algorithm failing to result in a single medication identifier match and in response to the application of the algorithm failing to result in a plurality of potential medication identifier matches. Example apparatuses may also receive a selection of one of the list of medication identifiers to be a determined medication identifier match and create a mapped product identifier to the determined medication identifier match in the database in response to receiving the selection of the determined medication identifier match. Causing the apparatus to receive a product identifier associated with a medication container may include causing the apparatus to scan a barcode from the medication container and decipher the barcode to obtain the product identifier.

Embodiments may provide for a computer program product including at least one non-transitory computer-readable storage medium having computer-executable program code instructions stored therein. The computer-executable program code instructions comprising program code instructions to receive a product identifier associated with a medication container; compare the product identifier with a database of product identifier formats; and retrieve a medication identifier corresponding to the product identifier in response to the product identifier corresponding with a mapped product identifier in the database. Embodiments may include program code instructions to apply an algorithm to the product identifier in response to the product identifier failing to correspond with a mapped product identifier in the database, and create a mapped product identifier to a single medication identifier match in the database in response to the application of the algorithm to the product identifier resulting in the single medication identifier match.

Embodiments may include program code instructions to generate a plurality of potential medication identifier matches in response to the product identifier corresponding to a plurality of product identifier formats in the database. Embodiments may include program code instructions to present the plurality of potential medication identifier matches to a user, receive a selection of one of the plurality of potential medication identifier matches to be a determined medication identifier match, and create a mapped product identifier to the determined medication identifier match in the database in response to receiving the selection of the determined medication identifier match. According to some embodiments, the computer program product may include program code instructions to generate a list of medication identifiers irrespective of the product identifier in response to the application of the algorithm failing to result in a single medication identifier match and in response to the application of the algorithm failing to result in a plurality of potential medication identifier matches. Embodiments may include program code instructions to receive a selection of one of the list of medication identifiers to be a determined medication identifier match, and create a mapped product identifier to the determined medication identifier match in the database in response to receiving the selection of the determined medication identifier match.

BRIEF DESCRIPTION OF THE DRAWINGS

Figure 1:
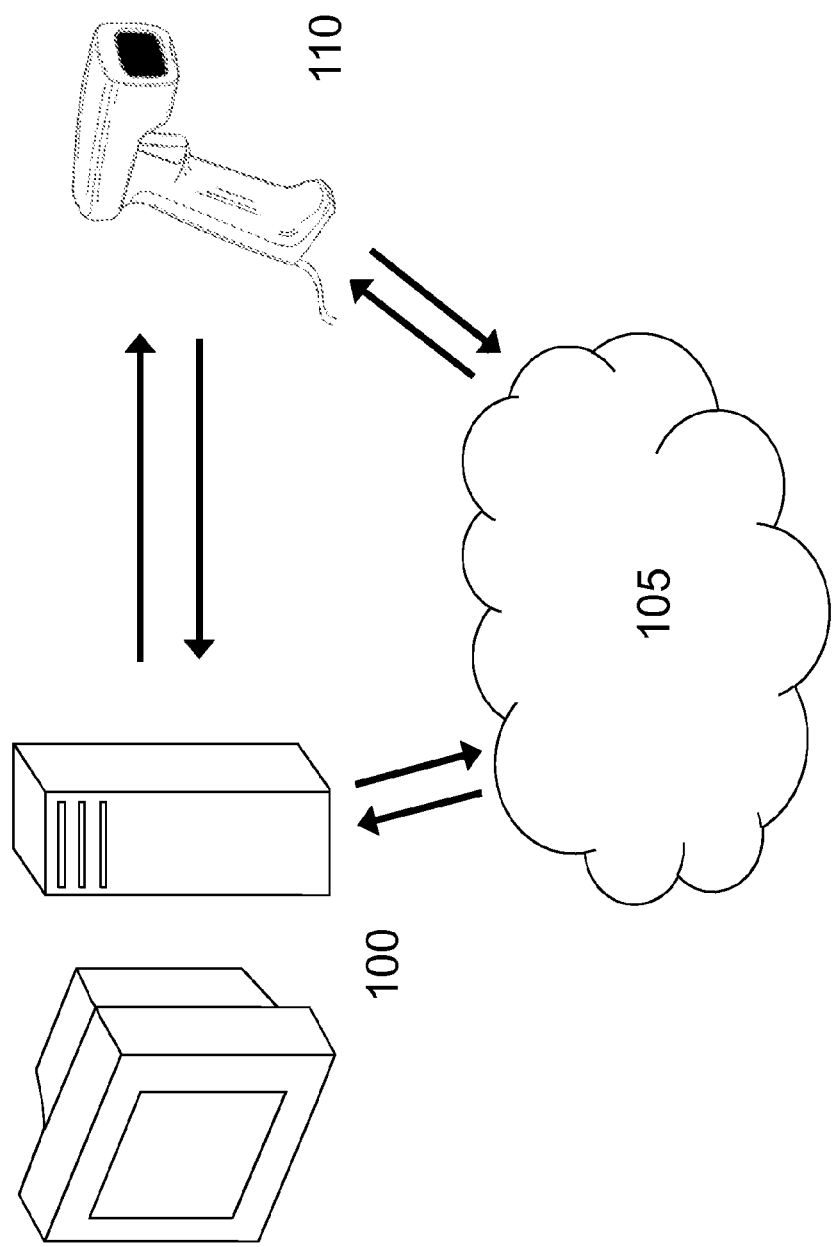
Figure 2:
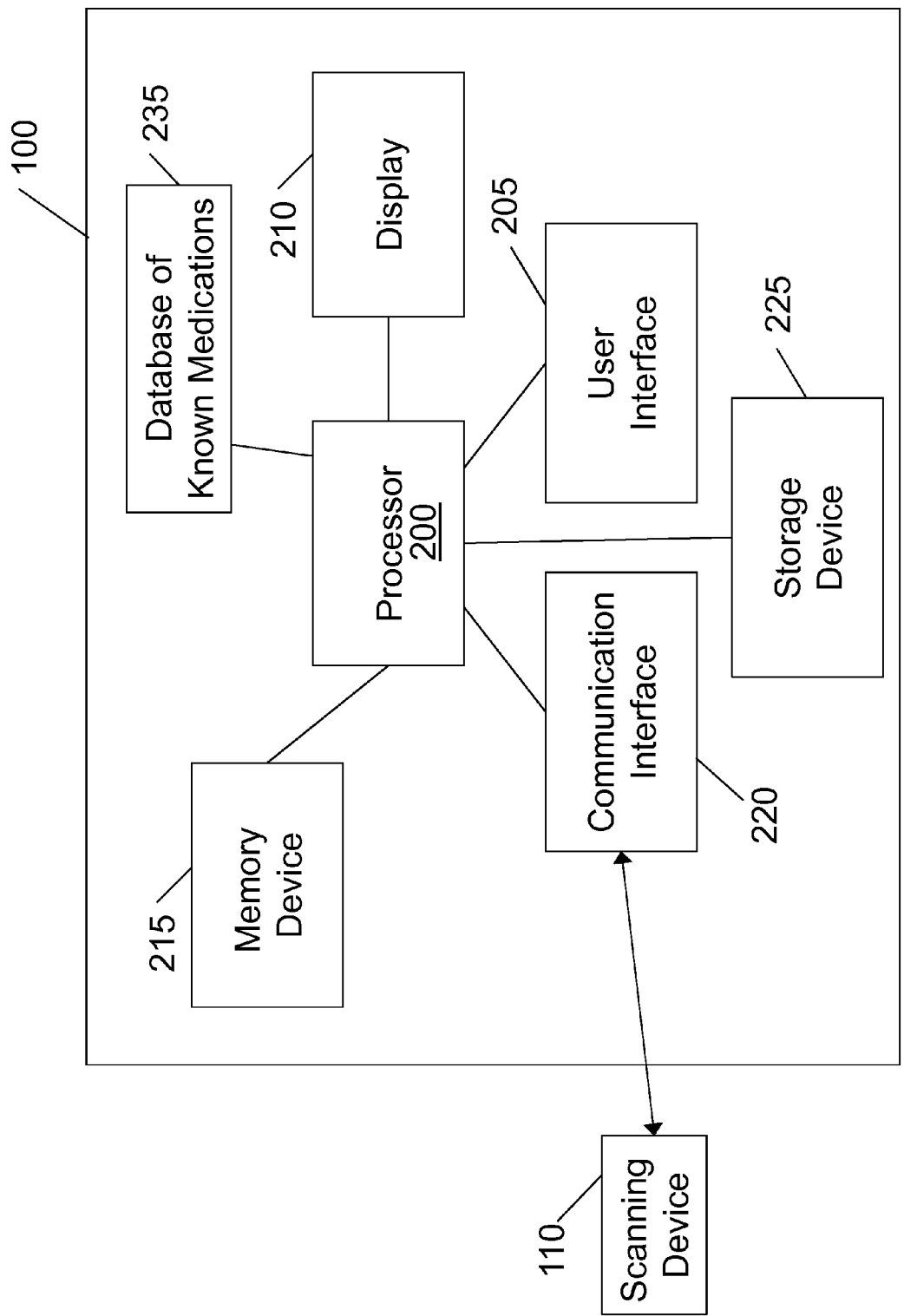
Figure 3:
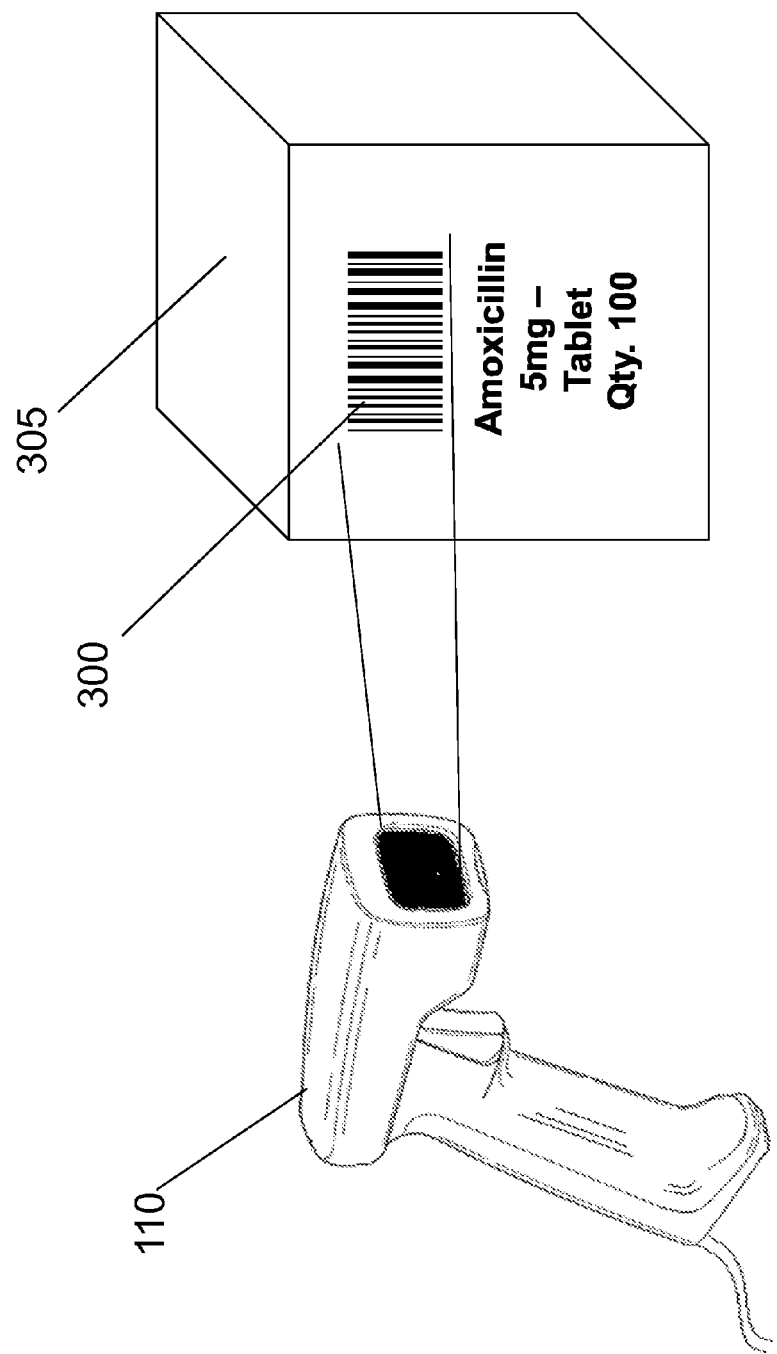
Figure 4:
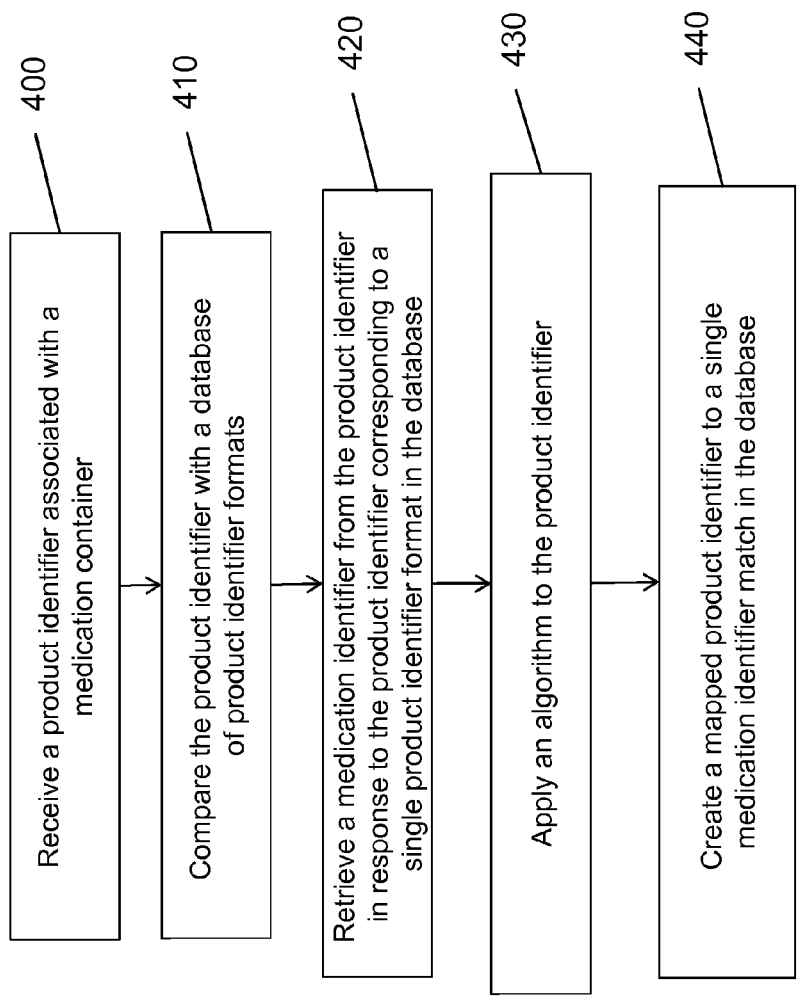

Having thus described certain example embodiments of the invention in general terms, reference will now be made to the accompanying drawings, which are not necessarily drawn to scale, and wherein:

FIG. 1 illustrates a system for mapping product identification to medication identification according to an example embodiment of the present invention;

FIG. 2 is a block diagram of various components of a system for mapping product identification to medication identification according to an example embodiment of the present invention;

FIG. 3 illustrates an example implementation of a system for mapping product identification to medication identification according to the present invention; and FIG. 4 is a flowchart of a method for mapping product identification to medication identification according to an example embodiment of the present invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

In general, example embodiments of the present invention provide a means for identifying medications received or processed through a healthcare facility or pharmacy. A pharmacy or healthcare facility may receive medications from a plurality of distributors or manufacturers where each medication package, or product, includes a product identifier, which may be unique to the specific product. The product identifier may be an identification which is associated with the product, such as a barcode printed on the product or affixed thereto, a radio frequency identification (RFID) tag associated with the product, or other identifying indicia which is used to identify the product.

Commercially available prescription medications may include a barcode which encodes a product identifier for the medication; however, the identifier may not always match the medication identifiers used by industry to identify the medication. With the advent of bedside barcoded administration systems to ensure patient safety, the disconnect between healthcare standard medication identifiers and product identifiers used on commercially packaged medications has been exacerbated. Users may be compelled to manually map the scanned barcode values (i.e., a product identifier) to a medication identifier, or rely on a software algorithm to try to identify the medication based on industry standards. The former method may be labor intensive and susceptible to human error which may be intensified by frequent shortages and medication substitutions from the commercial wholesaler. The latter solves many of the labor issues, but it may be slow to react to new or non-standard barcode formats. The latter may also require human intervention to address collisions that occur when a product identifier barcode could potentially identify two or more different medications based on the defined industry standards.

The term "product identifier" is used herein to describe the identification of a medication that is assigned by the commercial wholesaler or medication re-packager to identify the product. The term "medication identifier" is used herein to describe the identification of a medication that is conventional in the healthcare industry, such as a National Drug Code (NDC) identifier.

Described herein is a mechanism to combine a manual mapping solution with a software algorithm solution by allowing for the automated mapping of product identifier barcodes to medication identifiers using proprietary software algorithms to find the best candidate based on both standard and proprietary formats.

As should be appreciated, various embodiments may be implemented in various ways, including as methods, apparatus, systems, or computer program products. Accordingly, various embodiments may take the form of an entirely hardware embodiment or an embodiment in which a processor is programmed to perform certain steps. Furthermore, various implementations may take the form of a computer program product on a computer-readable storage medium having computer-readable program instructions embodied in the storage medium. Any suitable computer-readable storage medium may be utilized including hard disks, CD-ROMs, optical storage devices, or magnetic storage devices.

Various embodiments are described below with reference to block diagrams and flowchart illustrations of methods, apparatus, systems, and computer program products. It should be understood that each block of the block diagrams and flowchart illustrations, respectively, may be implemented in part by computer program instructions, e.g., as logical steps or operations executing on a processor in a computing system. These computer program instructions may be loaded onto a computer, such as a special purpose computer or other programmable data processing apparatus to produce a specifically-configured machine, such that the instructions which execute on the computer or other programmable data processing apparatus implement the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the functionality specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide operations for implementing the functions specified in the flowchart block or blocks.

Accordingly, blocks of the block diagrams and flowchart illustrations support various combinations for performing the specified functions, combinations of operations for performing the specified functions, and program instructions for performing the specified functions. It should also be understood that each block of the block diagrams and flowchart illustrations, and combinations of blocks in the block diagrams and flowchart illustrations, can be implemented by special purpose hardware-based computer systems that perform the specified functions or operations, or combinations of special purpose hardware and computer instructions.

FIG. 1 provides an illustration of an identification system that can be used in conjunction with various embodiments of the present invention. As shown in FIG. 1, an example embodiment of the identification system may include a scanning device 110, one or more networks 105, and a processing device 100. As illustrated, the scanning device 110 may be in wired or wireless communication with one or both of the network(s) 105 and the processing device 100. Embodiments may further include other network entities from which data may be received from or transmitted to, as will be described further below. Each of the components of the system may be in electronic communication with, for example, one another over the same or different wireless or wired networks (e.g., network 105) including, for example, a wired or wireless Personal Area Network (PAN), Local Area Network (LAN), Metropolitan Area Network (MAN), Wide Area Network (WAN), or the like. Additionally, while FIG. 1 illustrates the various system entities as separate, standalone entities, the various embodiments are not limited to this particular architecture.

FIG. 2 illustrates the various components of an example embodiment of the identification system of FIG. 1, including the scanning device 110 which may be in communication with the processor 200 of, for example, the processing device 100. The processor 200 may be embodied in a number of different ways. For example, the processor 200 may be embodied as a processing element, processing circuitry, a coprocessor, a controller or various other processing devices including integrated circuits such as, for example, an application specific integrated circuit (ASIC), a field programmable gate array (FPGA), a hardware accelerator, and/or the like.

In an example embodiment, the processor 200 may be configured to execute instructions stored in memory or otherwise accessible to the processor 200. As such, whether configured by hardware or software methods, or by a combination thereof, the processor 200 may represent an entity capable of performing operations according to embodiments of the present invention when configured accordingly. For example, as discussed in more detail below, the identification system may be configured, among other things, to facilitate accurate scanning and identification of medications as they are scanned either at a pharmacy, a patient bedside, a nurse station, or any other location where accurate identification of medication is necessary. A display 210 may be configured to present additional information to a user, such as the medication identification, dosage, destination, or other information to a healthcare provider. A user interface 205 may be configured for user input to confirm medication identification, initiate medication identification, or the like. The user interface 205 may include a touch screen, such as when the processing device is a tablet computer or portable computing apparatus or the user interface may include a keyboard and/or a pointing device, such as a mouse.

The identification system may further be in communication with a database of known medications 235 which may include identifying information regarding a plurality of medications, as described further below. The identification system may further include transitory and non-transitory memory device 215, which may include both random access memory (RAM) and read only memory (ROM). The ROM may be used to store a basic input/output system (BIOS) containing the basic routines that help to transfer information to the different elements within the identification system.

In addition, in one embodiment, the identification system may include at least one storage device 225, such as a hard disk drive, a CD drive, and/or an optical disk drive for storing information on various computer-readable media. The storage device(s) 225 and its associated computer-readable media may provide non-volatile storage. The computer-readable media described above could be replaced by any other type of computer-readable media, such as embedded or removable multimedia memory cards (MMCs), secure digital (SD) memory cards, Memory Sticks, electrically erasable programmable read-only memory (EEPROM), flash memory, hard disk, and/or the like. The storage device may be configured to store, for example, an audit trail of medications identified or mapped, operations, errors, alerts, and manual identification of product identifiers as described below.

Furthermore, a number of executable instructions, applications, scripts, program modules, and/or the like may be stored by the various storage devices 225 and/or within memory device 215. As discussed in more detail below, these executable instructions, applications, program modules, and/or the like may control certain aspects of the operation of the identification system with the assistance of the processor 200 and operating system, although their functionality need not be modularized. In addition to the program modules, the identification system may store or be in communication with one or more databases.

Also located within the identification system, in one embodiment, is a communication interface 220 for interfacing with various computing entities. This communication may be via the same or different wired or wireless networks (or a combination of wired and wireless networks). For instance, the communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the identification system 100 may be configured to communicate via wireless external communication networks using any of a variety of protocols, such as 802.11, general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), 802.16 (WiMAX), ultra wideband (UWB), infrared (IR) protocols, Bluetooth™ protocols, wireless universal serial bus (USB) protocols, and/or any other wireless protocol.

It will be appreciated that one or more of the identification system components may be located remotely from other identification system components. For example the scanning device 110 may be located or in communication with a remote network entity. Furthermore, one or more of the components may be combined and additional components performing functions described herein may be included in the identification system.

According to an example embodiment of the present invention, a user may use an embodiment of the identification system described above to scan a product identifier 300 encoded on a medication container 310, as illustrated in FIG. 3. While the embodiments disclosed herein describe and illustrate the scanning of a conventional barcode, it is appreciated that the product identification may be encoded onto a medication package through any available means, such as through a two-dimensional barcode, a radio frequency identification (RFID) tag, printed text characters, etc. The scanning device 110 of example embodiments may be configured to read any of these available encoding means, such as using a barcode scanner, an RFID reader, an image capture device with character recognition, or the like. As such, the embodiments illustrated herein are not intended to limit the mechanisms for encoding and reading the identification, but merely provide an example embodiment.

The scanning device 110, illustrated in FIG. 3, may send the scanned product identifier barcode information to the processing device 100. The scanning device 110 may provide interpretation of the scanned barcode, such as decoding the barcode into an alpha-numerical format, or the scanning device 110 may provide only interpreted scanned information to the processing device 100 for translation into the alpha-numeric format stored in the barcode. The processing system may then review the database of known medications 235 for an existing medication identifier corresponding to the product identifier. If a match exists between the product identifier and a medication identifier within the database of known medications 235, the identification system returns the mapped medication identifier. A product identifier with a known, mapped medication identifier is known as a "string literal" as the product identifier is literally interpreted as the medication identifier that is mapped thereto.

If the product identifier is unrecognized by the identification system (e.g., the product identifier is not mapped to a medication identifier in the database of known medications 235, i.e., no string literal), the identification system evaluates the product identifier against a library of standard and non-standard product identification formats to ascertain the medication identifier. Evaluating the product identifier against standard and non-standard formats includes analyzing the product identifier, and if a single product identifier format is found that corresponds to the product identifier, extracting a medication identifier (e.g., a National Drug Code, a Global Trade Identification Number (GTIN), etc.) from the product identifier. If a medication identifier is extracted from the product identifier, the product identifier may be subsequently mapped to the medication identifier and stored in the database of known medications 235 in order to create a string literal. Subsequent scanning of the same product code will more easily arrive at the medication identifier as the product identifier is a string literal to the medication identifier, and a medication identifier does not have to be extracted from the product code.

The extraction of a medication identifier from the product identifier using the plurality of standard or non-standard product identifier formats may be performed through one or more algorithms. The algorithms may compare the product identifier to known standard formats in order to determine a medication identifier, or portion thereof, contained within the product identifier. For example, several standard formats may include the standard formats of a National Drug Code (NDC). The NDC for a medication includes three distinct segments. The first segment is the labeler code. The second segment is the product code, and the third segment is the package code. The NDC may be either ten digits or eleven digits, with the labeler code being four or five digits, the product code being three or four digits, and the package code being one or two digits. Ten digit NDCs may be in the format of 4-4-2 (four digit labeler code, four digit product code, and two digit package code), 5-3-2, or 5-4-1. Eleven digit NDCs are in the format of 5-4-2 (five digit labeler code, four digit product code, and two digit package code). In order to convert a ten digit NDC to an eleven digit NDC, a zero pad must be added at either the first position (ahead of the 4-digit labeler code in a 4-4-2 format), the sixth position (ahead of the 3-digit product code in a 5-3-2 format), or the ninth position (ahead of the 1-digit package code in a 5-4-1 format). While an eleven digit NDC may be included in certain barcode formats (e.g., type 39), one of the more ubiquitous barcode formats, the Universal Product Code or UPC, is limited to a ten character product identifier, thus limiting the UPC to ten characters in which to encode an NDC. Thus, in order for an NDC to be extracted from a product code, an algorithm can be used to either extract an eleven digit NDC or to ascertain the format of a ten digit NDC in order to properly zero pad the NDC to an eleven digit format.

In an example embodiment of an algorithm to extract a medication identifier from a product identifier, the product identifier may be compared against a database of known product identifier formats. If the format of the product identifier corresponds with one of the known product identifier formats, the medication identifier may be extracted from the product identifier. The defined product identifier formats include a specific format and/or location within the product identifier that contains the medication identifier. Based on a determined product identifier format, the corresponding medication identifier can be easily extracted from the product identifier.

According to some embodiments, if the product identifier format corresponds to more than one product identifier format, a single medication identifier cannot be properly discerned. In such an instance, a medication identifier is extracted from the product identifier for each of the potential product identifier formats. This produces a list of medication identifiers which may correspond to the product identifier. In such an example, the multiple potential medication identifiers may be presented to a user, for example, on display 210, for the user to select the appropriate medication identifier, such as through user interface 205. If a user selects a medication identifier to correspond to the product identifier, the product identifier is mapped to the medication identifier in the database of known medications 235 to create a string literal for the product identifier, or the selected medication identifier may be referenced for future use with the product identifier. On any subsequent scanning of the same product identifier, the medication identifier will be known.

In another example embodiment, if a portion of a medication identifier, such as a product code is successfully extracted from a product identifier, but a labeler code or a package code cannot be discerned, embodiments may present a list of medication identifiers that include the appropriate product code, but have differing labeler codes and/or package codes in order for a user to select the appropriate medication identifier.

According to some embodiments, if the product identifier is of an unrecognized format and the identification system is unable to extract a medication identifier, and if the identification system is unable to provide potential medication identifiers that may match the product identifier, the identification system may provide a list of medications for a user to select from to map to the product identifier. This list of medications may be provided without regard to the product identifier since the product identifier failed to correspond with any unique medication identifiers or any potential medication identifiers. In response to a user selecting a medication identifier to correspond to the product identifier, a string literal for the product identifier and the medication identifier may be created as the product identifier is mapped to the medication identifier in the database of known medications 235.

FIG. 4 illustrates an example embodiment of a method for obtaining medication identification from product identification. A product identifier associated with a medication container is received at 400. The product identifier may be, for example, in the form of a barcode which may be scanned, or the product identifier may be encoded onto an RFID tag, which may be read. The scanned or read product identifier is received at 400. The product identifier format is compared with a database of known product identifier formats at 410. A medication identifier corresponding to the product identifier may be retrieved at 420 in response to the product identifier corresponding to a single product identifier format in the database. An algorithm may be applied to the product identifier at 430 in response to the product identifier failing to correspond to a product identifier format in the database. A mapped product identifier may be created in the database at 440 in response to the application of the algorithm to the product identifier resulting in the single medication identifier.

In an example embodiment, an apparatus for performing the method of FIG. 4 above may include a processor (e.g., the processor 200) configured to perform some or each of the operations (400-440) described above. The processor 200 may, for example, be configured to perform the operations (400-440) by performing hardware implemented logical functions, executing stored instructions, or executing algorithms for performing each of the operations. Alternatively, the apparatus may comprise means for performing each of the operations described above. In this regard, according to an example embodiment, examples of means for performing operations 400-440 may comprise, for example, the identification system (or respective different components thereof). Additionally or alternatively, at least by virtue of the fact that the processor 200 may be configured to control or even be embodied as the identification system, the processor 200 and/or a device or circuitry for executing instructions or executing an algorithm for processing information as described above may also form example means for performing operations 400-440.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method comprising:
receiving a product identifier associated with a medication container;
comparing the product identifier with a database of product identifier formats;
retrieving a medication identifier from the product identifier in response to the product identifier corresponding to a single product identifier format in the database;
applying an algorithm to the product identifier in response to the product identifier failing to correspond with a product identifier format in the database;
creating a mapped product identifier to a single medication identifier match in the database in response to the application of the algorithm to the product identifier resulting in the single medication identifier match; and
generating a plurality of potential medication identifier matches in response to the product identifier corresponding to a plurality of product identifier formats in the database.

2. The method of claim 1, further comprising:
presenting the plurality of potential medication identifier matches to a user.

3. The method of claim 2, further comprising:
receiving a selection of one of the plurality of potential medication identifier matches to be a determined medication identifier match; and
creating a mapped product identifier to the determined medication identifier match in the database in response to receiving the selection of the determined medication identifier match.

4. The method of claim 1, further comprising:
generating a list of medication identifiers irrespective of the product identifier in response to the application of the algorithm failing to result in a single medication identifier match and in response to the application of the algorithm failing to result in a plurality of potential medication identifier matches.

5. The method of claim 4, further comprising:
receiving a selection of one of the list of medication identifiers to be a determined medication identifier match; and
creating a mapped product identifier to the determined medication identifier match in the database in response to receiving the selection of the determined medication identifier match.

6. The method of claim 1, wherein receiving a product identifier associated with a medication container comprises scanning a barcode from the medication container and deciphering the barcode to obtain the product identifier.

7. An apparatus comprising at least one processor and at least one memory including computer program code, the at least one memory and the computer program code configured to, with the processor, cause the apparatus to at least:
    receive a product identifier associated with a medication container;
    compare the product identifier with a database of product identifier formats;
    retrieve a medication identifier from the product identifier in response to the product identifier corresponding to a single product identifier format in the database;
    apply an algorithm to the product identifier in response to the product identifier failing to correspond with a product identifier format in the database;
    create a mapped product identifier to a single medication identifier match in the database in response to the application of the algorithm to the product identifier resulting in the single medication identifier match; and
    generate a plurality of potential medication identifier matches in response to the product identifier corresponding to a plurality of product identifier formats in the database.

8. The apparatus of claim 7, wherein the apparatus is further caused to:
    present the plurality of potential medication identifier matches to a user.

9. The apparatus of claim 8, wherein the apparatus is further caused to:
    receive a selection of one of the plurality of potential medication identifier matches to be a determined medication identifier match; and
    create a mapped product identifier to the determined medication identifier match in the database in response to receiving the selection of the determined medication identifier match.

10. The apparatus of claim 7, wherein the apparatus is further caused to:
    generate a list of medication identifiers irrespective of the product identifier in response to the application of the algorithm failing to result in a single medication identifier match and in response to the application of the algorithm failing to result in a plurality of potential medication identifier matches.

11. The apparatus of claim 10, wherein the apparatus is further caused to:
    receive a selection of one of the list of medication identifiers to be a determined medication identifier match; and
    create a mapped product identifier to the determined medication identifier match in the database in response to receiving the selection of the determined medication identifier match.

12. The apparatus of claim 7, wherein causing the apparatus to receive a product identifier associated with a medication container comprises causing the apparatus to scan a barcode from the medication container and decipher the barcode to obtain the product identifier.

13. A computer program product comprising at least one non-transitory computer-readable storage medium having computer-executable program code instructions stored therein, the computer-executable program code instructions comprising program code instructions to:
    receive a product identifier associated with a medication container;
    compare the product identifier with a database of product identifier formats;
    retrieve a medication identifier from the product identifier in response to the product identifier corresponding to a single product identifier format in the database;
    apply an algorithm to the product identifier in response to the product identifier failing to correspond with a product identifier format in the database;
    create a mapped product identifier to a single medication identifier match in the database in response to the application of the algorithm to the product identifier resulting in the single medication identifier match; and
    generate a plurality of potential medication identifier matches in response to the product identifier corresponding to a plurality of product identifier formats in the database.

14. The computer program product of claim 13, further comprising program code instructions to:
    present the plurality of potential medication identifier matches to a user.

15. The computer program product of claim 14, further comprising program code instructions to:
    receive a selection of one of the plurality of potential medication identifier matches to be a determined medication identifier match; and
    create a mapped product identifier to the determined medication identifier match in the database in response to receiving the selection of the determined medication identifier match.

16. The computer program product of claim 13, further comprising program code instructions to:
    generate a list of medication identifiers irrespective of the product identifier in response to the application of the algorithm failing to result in a single medication identifier match and in response to the application of the algorithm failing to result in a plurality of potential medication identifier matches.

17. The computer program product of claim 16, further comprising program code instructions to:
    receive a selection of one of the list of medication identifiers to be the determined medication identifier match; and
    create a mapped product identifier to the determined medication identifier match in the database in response to receiving the selection of the determined medication identifier match.

\* \* \* \* \*